(12) United States Patent  
Silvian

(10) Patent No.: US 6,577,898 B2  
(45) Date of Patent: Jun. 10, 2003

(54) BI-DIRECTIONAL TELEMETRY SYSTEM AND METHOD FOR TRANSMITTING DATA AT HIGH TRANSMISSION RATE

(75) Inventor: Sergiu Silvian, La Crescenta, CA (US)

(73) Assignee: Pacesetter, Inc., Sylmar, CA (US)

( * ) Notice: Subject to any disclaimer, the term of this patent is extended or adjusted under 35 U.S.C. 154(b) by 133 days.

(21) Appl. No.: 09/844,190

(22) Filed: Apr. 26, 2001

(65) Prior Publication Data

US 2002/0183799 A1 Dec. 5, 2002

(51) Int. Cl.⁷ .............................................. A61N 1/36
(52) U.S. Cl. ........................................ 607/32; 607/60
(58) Field of Search .......................... 607/4, 5, 9, 32, 607/60; 128/903

(56) References Cited

U.S. PATENT DOCUMENTS

| | | | |
|---|---|---|---|
| 4,661,948 A | 4/1987 | Shapiro et al. | 370/77 |
| 4,847,617 A | 7/1989 | Silvian | 340/870.16 |
| 4,944,299 A | 7/1990 | Silvian | 128/419 |
| 4,947,407 A | 8/1990 | Silvian | 375/94 |
| 4,980,898 A | 12/1990 | Silvian | 375/59 |
| 5,901,246 A | 5/1999 | Hoffberg et al. | 382/209 |
| 5,926,065 A | 7/1999 | Wakai et al. | 329/304 |
| 5,967,989 A * | 10/1999 | Cimochowski et al. | 600/549 |
| 6,169,925 B1 * | 1/2001 | Villaseca et al. | 607/60 |
| 6,366,206 B1 * | 4/2002 | Ishikawa et al. | 340/573.1 |

* cited by examiner

Primary Examiner—Carl Layno

(57) ABSTRACT

A bi-directional telemetry system includes an implanted unit that allows a high-speed transfer of digital data with minimal complexity of the electronic circuitry. A corresponding external unit is capable of decoding the high-data-rate transmitted information and, in turn, communicates with the implanted unit using pulse amplitude modulation. The data transmission rate of the implanted unit to the external device is 32 kbps, a four-fold increase over conventional data transmission rates, without increasing the carrier frequency. To this end, the implanted unit using a modified implementation of the quadrature amplitude modulation (QAM) method that generates the required symbols from readily available squarewave signals. Simulated sinewaves are generated within the transmitter by an inverting amplifier stage with variable input resistance determined by a pair of switches that are ultimately controlled by 16 k and 32 k clocks in the implanted unit. Data is encoded by changing the amplitude and polarity of the simulated sinewaves. Quadrupling of the data rate is achieved by taking advantage of the orthogonality of I and Q components, whose phases are in quadrature.

34 Claims, 10 Drawing Sheets

BI-DIRECTIONAL TELEMETRY SYSTEM AND METHOD FOR TRANSMITTING DATA AT HIGH TRANSMISSION RATE

FIELD OF THE INVENTION

The present invention generally relates to cardiac pacemakers and other types of implantable medical devices that can be programmed and/or analyzed following implantation using an external diagnostic/programmer system. Particularly, the invention relates to a high-speed digital telemetry system that includes a transmitter and a corresponding external receiver, with the transmitter achieving high data transmission rate without significantly increasing the design complexity.

BACKGROUND OF THE INVENTION

Implantable devices are implanted in a human or animal for the purpose of performing a desired function. This function may be purely observational or experimental in nature, such as monitoring certain body functions; or it may be therapeutic or regulatory in nature, such as providing critical electrical stimulation pulses to certain body tissue, nerves or organs for the purpose of causing a desired response. Implanted medical devices such as pacemakers, perform both observational and regulatory functions, i.e., they monitor the heart to ensure it beats at appropriate intervals; and if not, they cause an electrical stimulation pulse to be delivered to the heart in an attempt to force the heart to beat at an appropriate rate.

In order for an implantable device to perform its functions at minimum inconvenience and risk to the person or animal within whom it is used, some sort of noninvasive telemetry means must be provided that allows data and commands to be easily exchanged between the implantable device and an external device. Such an external device, also known as a controller, programmer, or monitor, provides a convenient mechanism through which the operation of the implantable device can be controlled and monitored, and through which data sensed or detected by the implanted device can be transferred out of the implanted device to an external (non-implanted) location where it can be read, interpreted, or otherwise used in a constructive manner.

As the sophistication and complexity of implanted devices has increased in recent years, the amount of data that must be transferred between an implanted device and its accompanying external device or programmer, has also increased. This, in turn, has resulted in a search for ways to effectuate such a data transfer at high speed. Understandably, an implanted device, due to its limited physical dimensions, allows for limited complexity of the electronic circuitry it can incorporate. Thus, in order for an implantable telemetry system to meet its design goals, it must transfer data at a high speed while preserving the relative simplicity of the circuitry.

An exemplary conventional telemetry system with a data transfer speed of 8 kbps (kilobits-per-second), more exactly 8192 bps, is described in U.S. Pat. No. 4,944,299 to Silvian. That telemetry system uses a carrier frequency of 8192 Hz, a frequency selected to be higher than a computer monitor vertical sweep generator fundamental and its harmonics, and below the horizontal sweep generator fundamental. This choice is based on the presumption that the computer monitor represents the primary source of interference for the carrier frequency. This 8 kbps telemetry system uses 1 bit per symbol and further uses a combined Amplitude Modulation (AM) and Phase Shift Keyed (PSK) modulation to limit the necessary bandwidth.

While the design of such a system is advantageous, there still remains a need for a telemetry system that allows high data rate transfer of information, and that does not substantially increase the design complexity of the implantable device.

SUMMARY OF THE INVENTION

The present invention addresses the foregoing need by providing an improved telemetry system. According to a preferred embodiment, an implanted unit (IU) of the telemetry system allows a high-speed transfer of digital data with minimal complexity of the electronic circuitry. A corresponding external unit is capable of decoding the high-data-rate transmitted information and, in turn, communicates with the implanted unit using, for example, pulse amplitude modulation (PAM).

In the preferred embodiment, the implanted unit-to-external device data rate is 32768 bps (32 k), a four-fold increase over conventional data transmission rates, without increasing the carrier frequency. In particular, the 32 k data is transmitted by the implanted unit, using a unique implementation of the QAM (quadrature amplitude modulation) method. Whereas traditional implementations of the QAM scheme require complicated components such as sinewave carriers, multipliers and filters, the present invention generates the required symbols from squarewave signals that are readily available as digital signals.

In particular, the simulated sinewaves are generated within the transmitter by an inverting amplifier stage with variable input resistance determined by a pair of switches that are ultimately controlled by 16 k and 32 k clocks in the implanted unit. Data is, in turn, encoded by changing the amplitude and polarity of the simulated sinewaves. Quadrupling of the data rate is achieved, not by decreasing the symbol period or increasing the carrier frequency, but rather by taking advantage of the orthogonality of I and Q components, whose phases are in quadrature. By implementing a two-bit modulation capability within each of the two transmitters, four bits of information (Ibit1, Ibit0, Qbit1, Qbit0) are encoded during one symbol period of 122 µs (equal to 1/8192 Hz) are encoded in an I transmitter signal while Qbit1 and Qbit0 are encoded in the output signal of the transmitter Q, 90 degrees out of phase with the signals from the I transmitter. These signals are fed into a telemetry coil for transmission to the external device.

The I transmitter has two digital inputs, Ibit1 and Ibit0, each with a pair of possible values, a logic 0 or a logic 1. Corresponding values Qbit1, Qbit0 are encoded in the output of the Q transmitter. The effects are the same within the individual transmitters, and thus, the digital inputs may be referred to generically as Bit1 and Bit0. In a preferred embodiment, Bit1 determines the polarity of the simulated sinewave during the symbol period. Bit0 independently controls the amplitude of the output, resulting in an absolute peak (normalized) amplitude of 1 or 0.5. Therefore, it may be understood that during the symbol period the resulting, modulated, simulated sinewave produced by an individual transmitter may take on any one of four possible functional forms: sin (t+φ), −sin (t+φ), 0.5 sin (t+φ), or −0.5 sin (t+φ), depending on the logic values of Bit1 and Bit0, where "sin" is understood to be a symbolic representation of the simulated sinewave synthesized from squarewaves, and φ represents the relative phase of the synthesized sinewaves. Phase quadrature between the signals produced by the two transmitters allows the embedded information to be distinguished and decoded by the external device.

In an exemplary implementation, the I transmitter and Q transmitter are identical. Phase quadrature, as required by the QAM method of the present invention, is achieved by including an inverter and a D flip-flop within the integrated circuit but external to the Q transmitter. Both the I and Q carrier frequencies are 8192 Hz and are, thus, equal to the conventional carrier/symbol rate. Higher frequency clocks of 8 k (8192 Hz), 16 k (16384 Hz), and 32 k (32768 Hz) that are required for this implementation, are generated from a 32 k crystal oscillator and by a chain of dividers.

Another important feature of the present invention is the novel implementation of symbol delimiters (start, end). By shifting both the I and Q symbol starting points 45 degrees with respect to the 8 k clock, the noise due to harmonics, generated by squarewaves, can be reduced. Thus, at both the symbol start and stop the worst-case amplitude jump is reduced and, in fact, is the same for both I and Q components.

In order to implement the foregoing design change on a conventional QAM scheme, a full amplitude, I transmitter-only signal is sent during a brief portion of the signal period. This allows a phase lock loop (PLL) in the external device to lock onto the exact phase of the I signal and thus discriminate its information from that of the Q signal. The full amplitude signal also allows the automatic gain control (AGC) within the external device to be simplified in its implementation, since it is able to lock onto a signal with no interference, with a larger magnitude and a larger signal-to-noise ratio.

In one embodiment, the external device (programmer)-to-IU data transfer rate will remain 8 kbps and will employ pulse amplitude modulation (PAM). However, to be fully compatible with the present implanted unit, a digital signal processing telemetry module (DTM) that forms part of the external device, can be modified to process QAM signals.

BRIEF DESCRIPTION OF THE DRAWINGS

The various features of the present invention and the manner of attaining them will be described in greater detail with reference to the following description, claims, and drawings, wherein reference numerals are reused, where appropriate, to indicate a correspondence between the referenced items, in which:

DETAILED DESCRIPTION OF THE INVENTION

The following description is of a best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
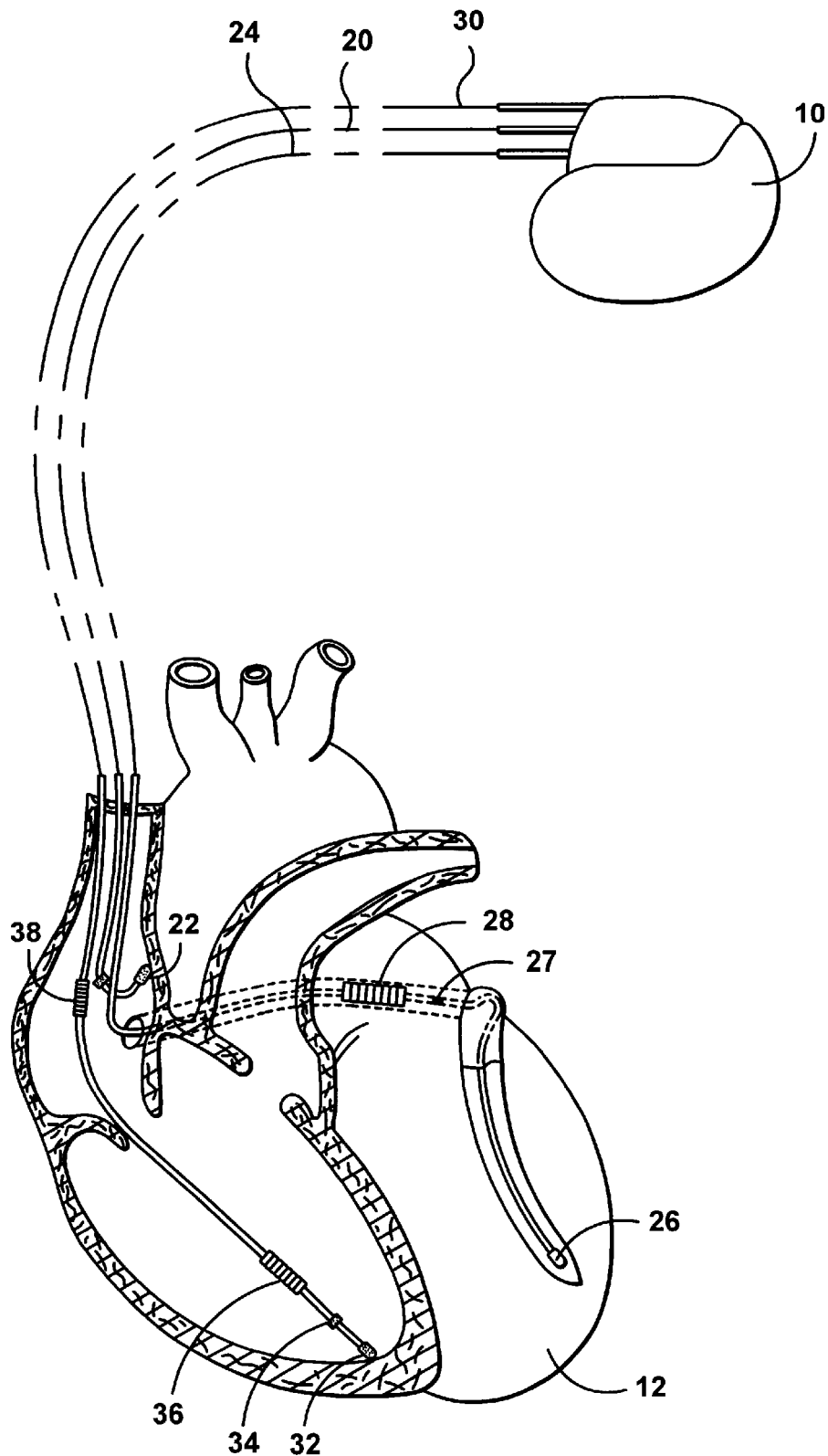
FIG. 1 is a simplified, partly cutaway view illustrating an implantable stimulation device in electrical communication with at least three leads implanted into a patient's heart for delivering multi-chamber stimulation and shock therapy.

FIG. 1 illustrates a stimulation device 10 in electrical communication with a patient's heart 12 by way of three leads 20, 24 and 30 suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left-chamber pacing therapy, the stimulation device 10 is coupled to a "coronary sinus" lead 24 designed for placement in the "coronary sinus region" via the coronary sinus os so as to place a distal electrode adjacent to the left ventricle and additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, the coronary sinus lead 24 is designed to receive atrial and ventricular cardiac signals and to deliver: left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode 36 will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
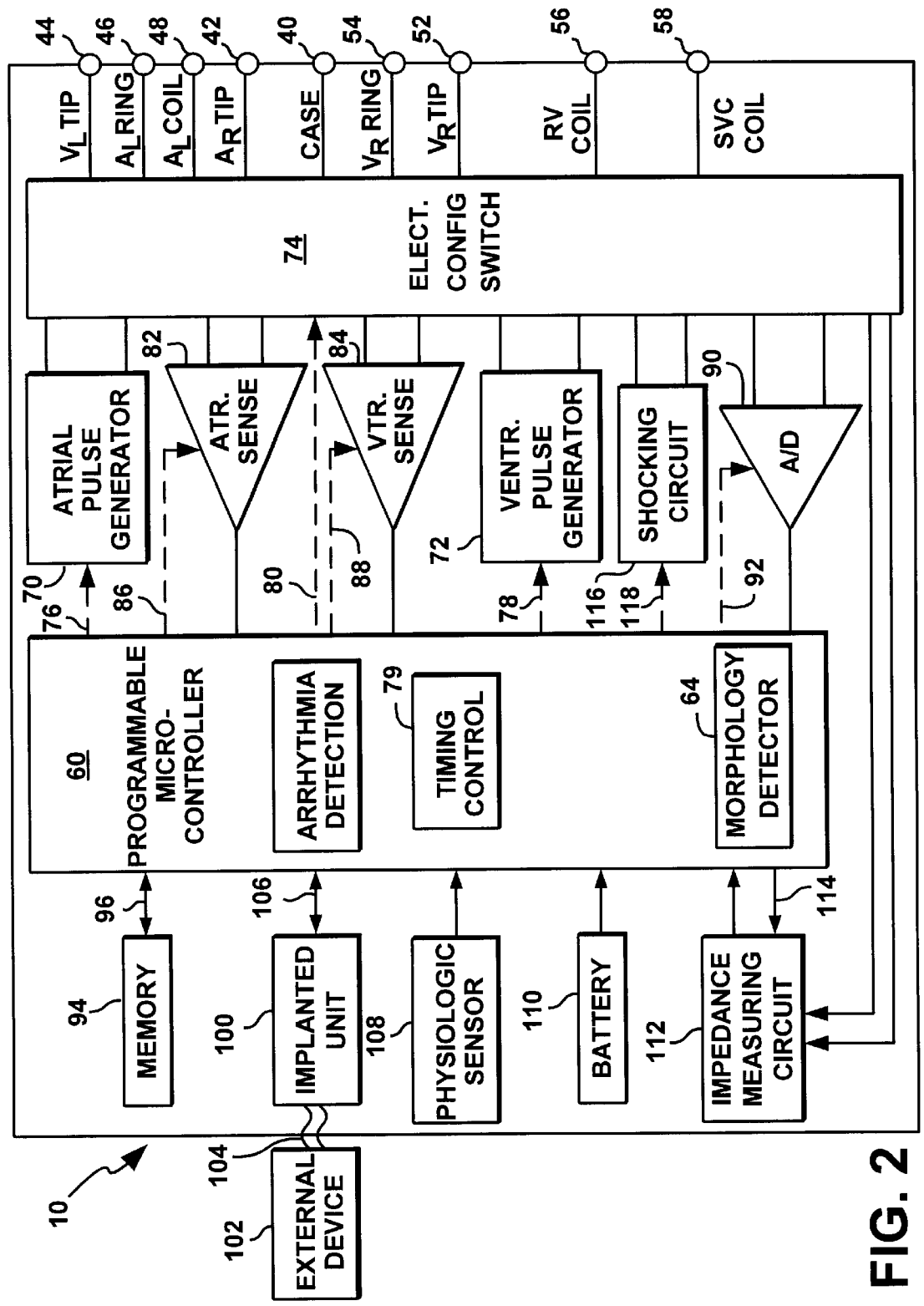
FIG. 2 is a functional block diagram of the multi-chamber implantable stimulation device of FIG. 1, illustrating the basic elements that provide cardioversion, defibrillation and/or pacing stimulation in four chambers of the heart, shown in telemetry communication with an external device/programmer.

FIG. 2 illustrates a simplified block diagram of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chambers or chambers with cardioversion, defibrillation and/or pacing stimulation.

The stimulation device 10 includes a housing 40 which is often referred to as "can", "case" or "case electrode", and which may be programmably selected to act as the return electrode for all "unipolar" modes. The housing 40 may further be used as a return electrode alone or in combination with one or more of the coil electrodes 28, 36, or 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal 42 adapted for connection to the atrial ($A_R$) tip electrode 22.

To achieve left chamber sensing, pacing and/or shocking, the connector includes at least a left ventricular ($V_L$) tip terminal 44, a left atrial ($A_L$) ring terminal 46, and a left atrial ($A_L$) shocking terminal (coil) 48, which are adapted for connection to the left ventricular tip electrode 26, the left atrial tip electrode 27, and the left atrial coil electrode 28, respectively.

To support right chamber sensing, pacing and/or shocking, the connector further includes a right ventricular ($V_R$) tip terminal 52, a right ventricular ($V_R$) ring terminal 54, a right ventricular (RV) shocking terminal (coil) 56, and an SVC shocking terminal (coil) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 that controls the various modes of stimulation therapy. As is well known in the art, the microcontroller 60 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via a switch bank 74. It is understood that in order to provide stimulation therapy in each of the four chambers of the heart, the atrial pulse generator 70 and the ventricular pulse generator 72 may include dedicated, independent pulse generators, multiplexed pulse generators, or shared pulse generators. The atrial pulse generator 70 and the ventricular pulse generator 72 are controlled by the microcontroller 60 via appropriate control signals 76 and 78, respectively, to trigger or inhibit the stimulation pulses.

The microcontroller 60 further includes timing control circuitry 79 which is used to control the timing of such stimulation pulses (e.g. pacing rate, atrio-ventricular (AV) delay, atrial interconduction (A—A) delay, or ventricular interconduction (V—V) delay, etc.), as well as to keep track of the timing of refractory periods, PVARP intervals, noise detection windows, evoked response windows, alert intervals, marker channel timing, etc.

The switch bank 74 includes a plurality of switches for connecting the desired electrodes to the appropriate I/O circuits, thereby providing complete electrode programmability. Accordingly, the switch bank 74, in response to a control signal 80 from the microcontroller 60, determines the polarity of the stimulation pulses (e.g. unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch bank 74, for detecting the presence of cardiac activity in each of the four chambers of the heart.

Cardiac signals are applied to the inputs of an analog-to-digital (A/D) data acquisition system 90. The data acquisition system 90 is configured to acquire intracardiac electrogram signals, convert the raw analog data into digital signals, and store the digital signals for later processing and/or telemetric transmission to an external device 102. The data acquisition system 90 is coupled to the right atrial lead 20, the coronary sinus lead 24, and the right ventricular lead 30 through the switch bank 74 to sample cardiac signals across any pair of desired electrodes. Advantageously, the data acquisition system 90 may be coupled to the microcontroller 60 or another detection circuitry, for detecting an evoked response from the heart 12 in response to an applied stimulus, thereby aiding in the detection of "capture".

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the stimulation device 10 may be non-invasively programmed into the memory 94 through an implanted unit (IU) 100 in telemetric communication with the external device 102, such as a programmer, transtelephonic transceiver, or a diagnostic system analyzer. The implanted unit 100 is activated by the microcontroller 60 by a control signal 106. The implanted unit 100 advantageously allows intracardiac electrograms and status information relating to the operation of the stimulation device 10 (as contained in the microcontroller 60 or memory 94) to be sent to the external device 102 through the established communication link 104.

The stimulation device 10 additionally includes a power source such as a battery 110 that provides operating power to all the circuits shown in FIG. 2. For the stimulation device 10, which employs shocking therapy, the battery 110 must be capable of operating at low current drains for long periods of time, and also be capable of providing high-current pulses (for capacitor charging) when the patient requires a shock pulse. The battery 110 must preferably have a predictable discharge characteristic so that elective replacement time can be detected. Accordingly, the stimulation device 10 can employ lithium/silver vanadium oxide batteries.

The stimulation device 10 further includes a magnet detection circuitry (not shown), coupled to the microcontroller 60. The purpose of the magnet detection circuitry is to detect when a magnet is placed over the stimulation device 10, which magnet may be used by a clinician to perform various test functions of the stimulation device 10 and/or to signal the microcontroller 60 that an external programmer 102 is in place to receive or transmit data to the microcontroller 60 through the implanted unit 100.

As further shown in FIG. 2, the stimulation device 10 is shown as having an impedance measuring circuit 112 which is enabled by the microcontroller 60 by a control signal 114. The impedance measuring circuit 112 is advantageously coupled to the switch bank 74 so that any desired electrode may be used.

It is a primary function of the stimulation device 10 to operate as an implantable cardioverter/defibrillator (ICD) device. That is, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5–10 Joules), or high (11 to 40 Joules) energy, as controlled by the microcontroller 60. Such shocking pulses are applied to the patient's heart through at least two shocking electrodes, and as shown in this embodiment, selected from the left atrial coil electrode 28, the RV coil electrode 36, and/or the SVC coil electrode 38 (FIG. 1). As noted above, the housing 40 may act as an active electrode in combination with the RV electrode 36, or as part of a split electrical vector using the SVC coil electrode 38 or the left atrial coil electrode 28 (i.e., using the RV electrode as common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asychronously (since R-waves may be too disorganized), and pertaining exclusively to the treatment of fibrillation. Accordingly, the microcontroller 60 is capable of controlling the synchronous or asynchronous delivery of the shocking pulses.

Figure 3:
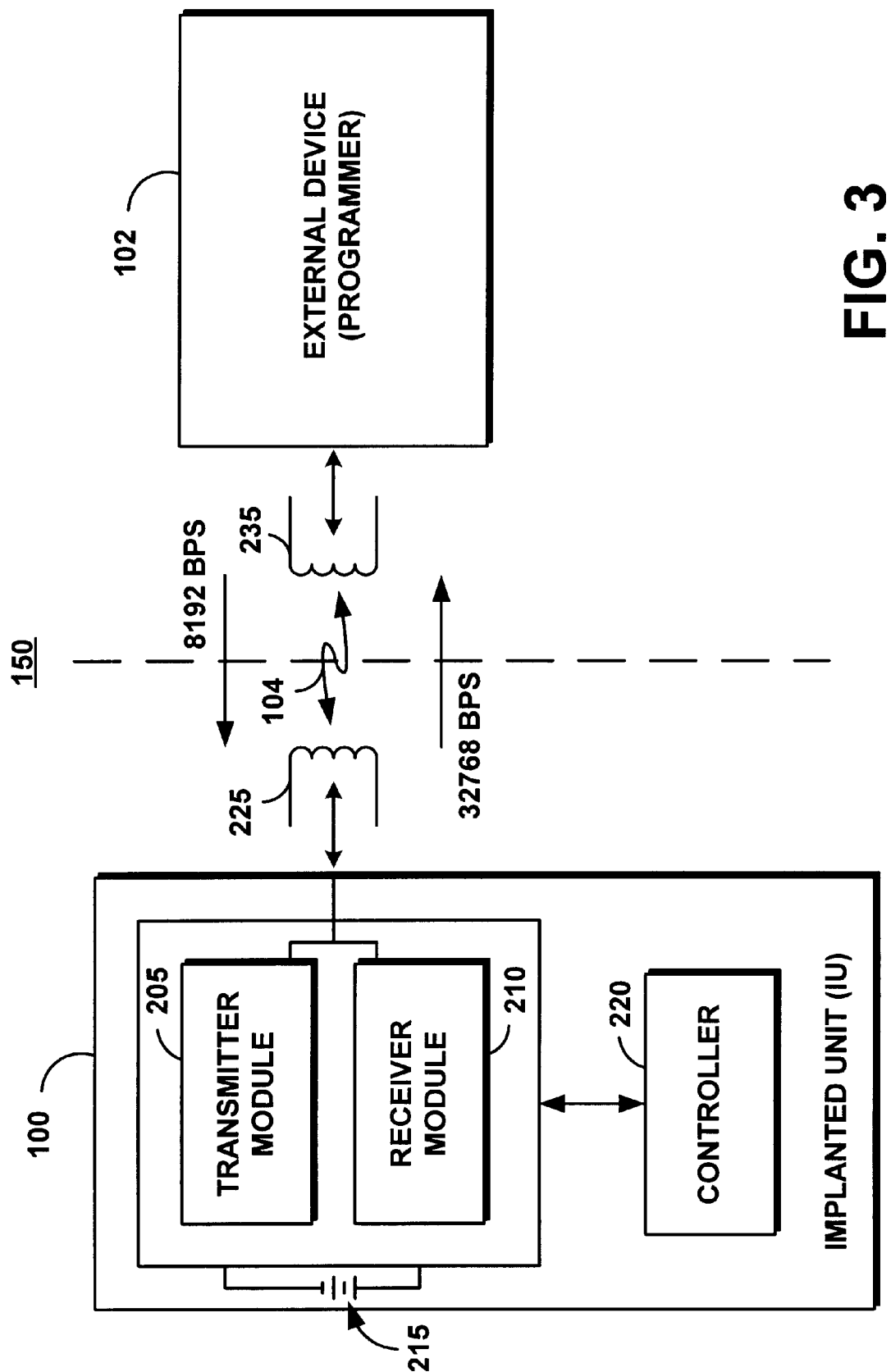
FIG. 3 is a high level block diagram of a telemetry system of the present invention, illustrating the building blocks of an implanted unit (IU) and the interchange of data between the implanted unit and an external device.

FIG. 3 is a high level block diagram of a telemetry system 150 of the present invention, which is comprised of the implanted unit 100 and the external device 102, each capable of communicating with the other via a telemetry link 104. The implanted unit 100 includes a transmitter module 205, whose elements are capable of producing a pair of signals in phase quadrature, a receiver module 210, a power source 215, a controller 220, and a telemetry coil 225.

In a preferred embodiment, digital information, encoded on a pair of orthogonal simulated sinewaves generated within the transmitter module 205, is sent to the external device 102 at a data rate of 32768 bps, using the modified quadrature amplitude modulation (QAM) method of the present invention.

Signals are transmitted from the implanted unit 100 to the external device 102 in the form of an electromagnetic wave via the telemetry coil 225. The external device 102 receives and transmits data via a telemetry coil 235. The transmission data rate of the external device 102 is 8192 bps while it is capable of receiving data at 32768 bps. The implanted unit 100 is capable of receiving pulse amplitude modulated data from the external device 102 at 8192 bps. Data is received by the implanted unit 100 via the telemetry coil 225 and the receiver module 210.

Figure 4A:
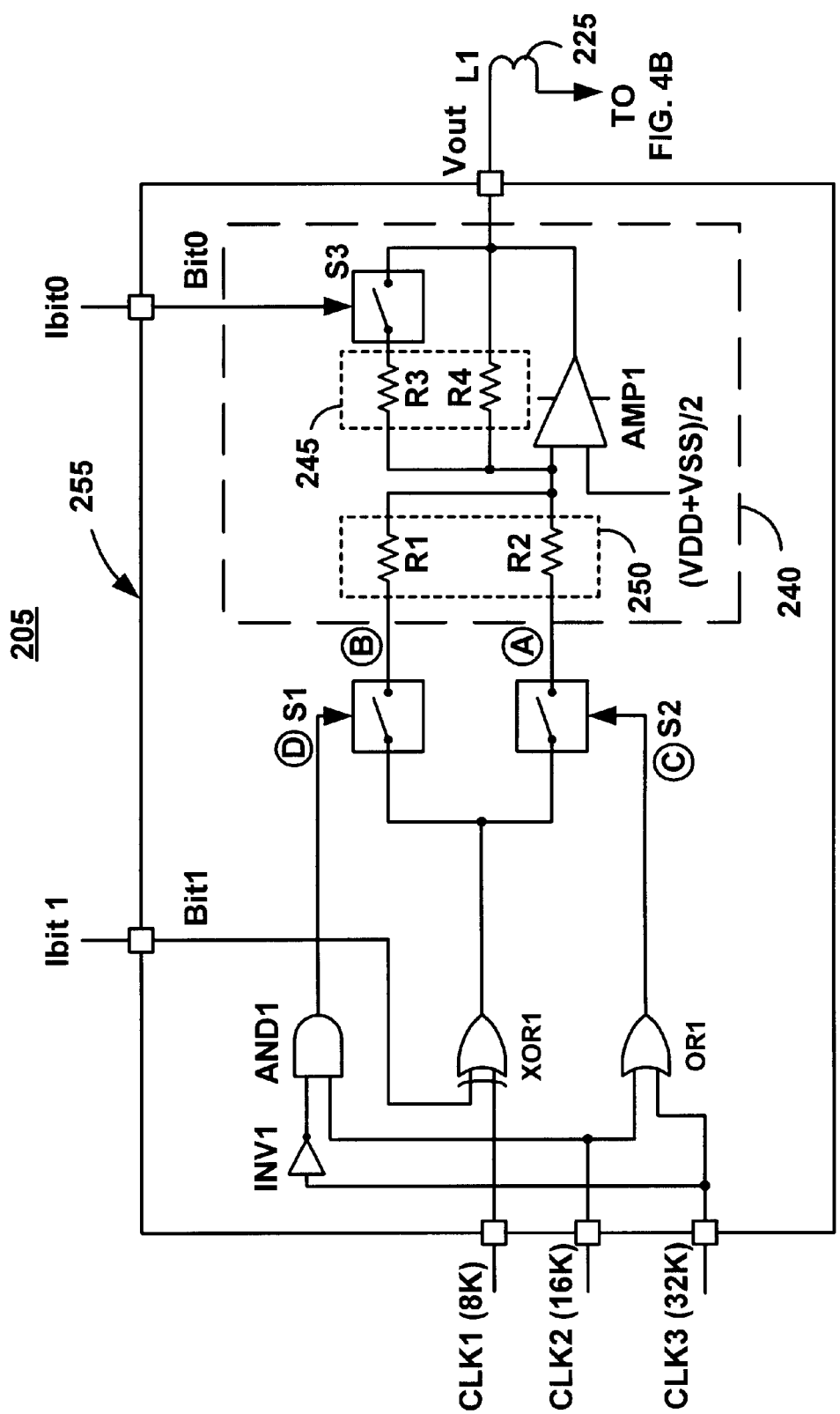
FIG. 4 is comprised of FIGS. 4A and 4B, and depicts a schematic representation of an I transmitter and a Q transmitter forming part of the implanted unit of FIG. 3, to illustrate the basic components that effect high-speed data transfer between the implanted unit and the external device.
Figure 4B:
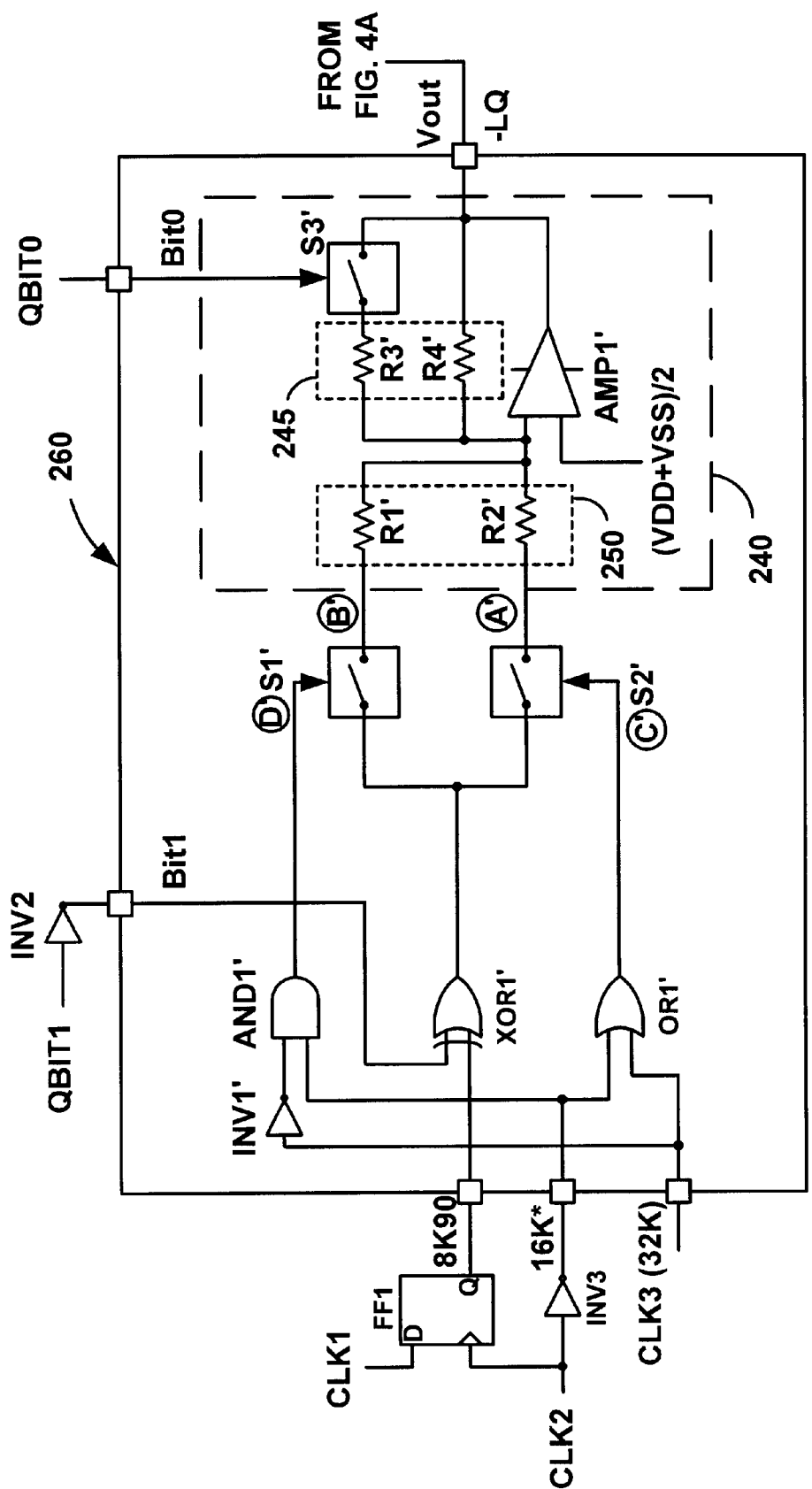

FIGS. 4A and 4B represent a more detailed schematic representation of the transmitter module 205 of FIG. 3, along with the telemetry coil 225 of FIG. 3. The transmitter module 205 includes analog and digital circuits that are readily implemented as components of an integrated circuit. The transmitter module 205 is generally comprised of two main components: an I transmitter 255 (FIG. 4A) and a Q transmitter 260 (FIG. 4B). For clarity and ease of explanation, only the I transmitter 255 will be described in detail, it being understood that the Q transmitter 260 is typically similar to the I transmitter 255 in function, design, and operation as a means of achieving phase quadrature.

With reference to FIG. 4A, the I transmitter 255 includes an inverter INV1, an AND gate AND1, an exclusive-OR gate XOR1, an OR gate, OR1, three switches, S1, S2 and S2, an amplifier AMP1, and four resistors, R1, R2, R3 and R4. Inputs to the I transmitter 255 include three clock signals, CLK1 (8 k), CLK2 (16 k) and CLK3 (32 k). It should be understood that the term 8 k is actually 8192 Hz (or 8×1024 Hz, where 1024 is "digital" thousand). The higher frequency clocks of 16 k (16384 Hz), 32 k (32768 Hz), required for this implementation, are generated from a 32 k crystal oscillator and dividers (not shown). The clock signals CLK1, CLK2 and CLK3 represent the squarewave signals which are converted into simulated sinewave symbols by means of a modified quadrature amplitude process.

As noted earlier, the Q transmitter 260 include similar components as the I transmitter 255 that are denoted by the primed designators corresponding to those in FIG. 4A, along with an inverter INV2 used to produce an inversion of Qbit1, and an inverter INV3 used in conjunction with a D-flip-flop FF1 to effect the condition of phase quadrature, or equivalently, a 90 degree phase shift in the output waveforms with respect to the I transmitter 255.

Having described the main components of the I transmitter 255 and the Q transmitter 260, their signal processing functions will now be described. Two digital signals serve as inputs to each transmitter. In the following description, these digital signals will be referred to as Ibit1 and Ibit0, for simplicity of illustration. These digital signals may be more generally referred to as Bit1 and Bit0, respectively, and may serve the same function within the Q transmitter as Qbit1 and Qbit0.

Signals Ibit1 and Ibit0 are used as inputs to determine the polarity and magnitude, respectively, of the output of the I transmitter 255. These digital inputs may be understood to represent the digital information that is encoded in the respective output signals of the two transmitters and, in an exemplary embodiment of this invention, are the sources of the modulation of the carrier signal.

In particular, two bits of information are encoded on each of the two carrier signals during a given signal period or symbol. These two bits are, in turn, fed into the telemetry coil 225 for transmission to the external device 102. The sum of the signals originating at the I and Q transmitters 255, 260, respectively, and appearing as excitation to the telemetry coil 225, is the QAM representation of the digital information sources in the implanted unit 100. In particular, the summed signal on the telemetry coil 225 is given by the following expression:

$$V_L = V_{LI} - (-V_{LQ}) = V_{LI} + V_{LQ},$$

where $V_L$ is the total voltage appearing across the telemetry coil 225, $V_{LI}$ is the voltage across the telemetry coil 225 due to the I transmitter 255, and $V_{LQ}$ is the voltage across the telemetry coil 225 due to the Q transmitter 260 output $-V_{LQ}$. The telemetry coil 225 then propagates the signals to the external device 102 in the form of an electromagnetic wave.

In conventional QAM methods, a pair of precisely generated sinewaves, in phase quadrature, are amplitude modulated to encode information. In the modified QAM of the present invention, simulated sinewaves are synthesized from squarewaves generated by means of digital circuitry used in conjunction with an amplifier gain stage with variable gain. Modulation is achieved by changing the amplitude and polarity of the simulated sinewave with binary inputs. These binary inputs remain either HIGH or LOW during the entire symbol period of, for example, 122 microseconds.

The operation of the individual components of the transmitter 205 will now be explained: Power to the transmitter 205 is provided by a DC supply, typically a battery, whose positive potential is represented by Vdd and the negative potential is represented by Vss. Thus, the total applied potential to the circuit is given by the difference of Vdd and Vss, i.e., Vdd−Vss. Logic gates within the circuit produce logic HIGHs at a voltage level equal to Vdd, while logic LOWs are equal to Vss. It should be clear that Vss may be equal to zero or even negative.

The amplifier AMP1 of FIG. 4A is connected to a resistive network comprised of resistors R1, R2, R3 and R4, to form an inverting amplifier gain stage 240. The variable, discrete gain of the amplifier AMP1 is determined by the relative values of a feedback resistance 245 (comprised of R3 and R4, as explained below), and an input resistance 250 (comprised of R1 and R2, as explained below). In particular, the gain "G" of the amplifier stage 240 is given by the following expression:

$$G = -R_b/R_a,$$

where $R_b$ is the resistance of the feedback resistance 245 and $R_a$ is the resistance of the input resistance 250.

The feedback resistance 245 may include resistor R4 alone or the parallel combination of resistors R3 and R4. Resistor R3 may be switched into, or out of the feedback loop 245 by closing or opening switch S3, as determined by the state of Ibit0. When S3 is closed, that is, when the input to switch S3 is a logic HIGH, resistor R3, equal to, and in parallel with resistor R4, reduces the impedance of the feedback loop by a factor of two, thus changing the output voltage of the amplifier AMP1 by the same factor.

Similarly, the input resistance 250 of the amplifier gain stage 240 may include resistor R2 alone (when S2 is closed and switch S1 is open), or the parallel combination of R1 and R2 (when both switches S1 and S2 are closed), or an open circuit (when both switches S1 and S2 are open).

The parallel combination of resistors R1 and R2 has the same resistance value as R4, and occurs when logic HIGHs are applied to the control inputs of S1 and S2, i.e., at the nodes labeled D and C, respectively. The open circuit case occurs when both switches S1 and S2 are open as a result of the outputs of the AND gate AND1 and the OR gate OR1 being both logic LOWs. In the case where both switches S1 and S2 are open, the gain of the amplifier gain stage 240 is equal to zero and the DC bias of the non-inverting terminal appears on the output.

The states of switches S1 and S2 are controlled exclusively by the 16 k clock CLK2 and the 32 k clock CLK3. Thus, the two switches S1 and S2 are completely independent of Ibit1 and Ibit0 The ultimate function of the two switches S1 and S2 is to change, in a repeatable and discrete fashion, the input resistance 250 of the amplifier gain stage 240, thus, producing a simulated sinewave, as synthesized with squarewaves. The 16 k and 32 k clocks divide the 8 k period, or one symbol time of 122 μs in 8 equal portions (or slices) to simulate a piecewise sinewave.

Switch S1 is controlled by the AND gate AND1, ultimately deriving its inputs from the 16 k clock CLK2 and 32 k clock CLK3. Switch S1 closes when the voltage at node D is a logic HIGH, that is when CLK3 is LOW and CLK2 is HIGH. Thus, switch S1 is closed for only one quarter-period during each cycle of the 8 k clock CLK1.

Switch S2 is controlled by the output of the OR gate OR1, which also derives its output from the 16 k clock CLK2 and the 32 k clock CLK3. The OR gate OR1 is HIGH for 3 quarters during a cycle of the 8 k clock CLK1. Using this logic sequence, the amplifier gain stage 240 is able to produce a simulated sinewave, synthesized from squarewaves with the synthesized wave containing discrete (normalized) levels: 0, +/−0.725, and +/−1.

The preceding analysis does not include the effects of changes in the output state of the exclusive-OR gate XOR1. It further presumes that switch S3 remains open. When S3 is closed, the gain of the amplifier gain stages is reduced by half and the corresponding levels are 0, +/−0.362, and +/−0.5).

The synthesis with switch S3 open and XOR1 constant, produces the values summarized in Table 1 below. For clarity, the piecewise-synthesized sinewave is displayed as a temporal waveform in FIG. 5A. In Table 1 below, H indicates a logic HIGH, L indicates a logic LOW, C indicates that a switch is CLOSED, O indicates that a switch is OPEN, |G| indicates the absolute value of the gain of the amplifier gain stage 240, and Vout indicates the normalized output of the amplifier gain stage 240. With S3 closed, the gain is reduced by half.

TABLE 1

| Slice | CLK1 | CLK2 | CLK3 | C | D | S1 | S2 | |G| | Vout |
|---|---|---|---|---|---|---|---|---|---|
| 1 | L | L | L | L | L | O | O | 0 | 0 |
| 2 | L | L | H | H | L | C | O | .725 | −.725 |
| 3 | L | H | L | H | H | C | C | 1 | −1.0 |
| 4 | L | H | H | H | L | C | O | .725 | −.725 |
| 5 | H | L | L | L | L | O | O | 0 | 0 |
| 6 | H | L | H | H | L | C | C | .725 | .725 |
| 7 | H | H | L | H | H | C | O | 1 | 1.0 |
| 8 | H | H | H | H | L | C | O | .725 | .725 |

In a preferred embodiment, the non-inverting terminal of the amplifier AMP1 is biased with a non-zero voltage equal to (Vdd+Vss)/2, thus placing its potential midway between the logic HIGH and logic LOW of the digital gates. By providing this mid-potential bias to the non-inverting terminal of the amplifier AMP1, the polarity of the output may be changed without affecting the magnitude of the signal. In particular, the polarity of the output is determined by logic state of the Exclusive-OR XOR1, with a logic HIGH (equal to Vdd) resulting in a negative output, and a logic LOW (Vss) resulting in a positive output. With all other conditions remaining unchanged, the magnitude of the voltage appearing across the input resistance 250 is the same whether the exclusive OR gate XOR1 is HIGH or LOW. It follows that the magnitude of the output voltage is also the same. The implication is that the polarity of the simulated sinewave may be changed without affecting its amplitude.

The exclusive-Or gate XOR1 has two inputs, the 8 k clock (CLK1) and the Ibit1 inputs. The logic of an exclusive-OR is such that the output of the gate is HIGH when either, but not both, of the inputs is a logic HIGH. Thus, with Ibit1 held LOW, the output of the exclusive-OR XOR1 follows the state of the 8 k Clock CLK1. With the Ibit1 input held HIGH, the output is an inversion of the 8 k clock CLK1. In either case, with Ibit1 held constant, the output of XOR1 alternates between HIGH and LOW states each 8 k cycle, changing states when the 8 k clock CLK1 changes states. Referring to Table 1 above, it can be seen that the sequence produced by switches S1 and S2, combined with the functionality of XOR1 produces a simulated sinewave Vout with a fundamental period of 122 microseconds, which is the period of the 8 k clock and of the communication symbol (the waveshape transmitted during one 8 k period).

In general, the state of Ibit1 is not held constant but rather reflects the binary value of the information to be relayed to the external device 102. In this general case, the state of the exclusive-OR XOR1, and thus, the polarity of the output of the amplifier gain stage 240 is controlled by Ibit1. When Ibit1 is a logic HIGH, the 8 k Clock is inverted. When Ibit1 is a logic LOW, the clock signal is transmitted directly to the inverting terminal of the amplifier AMP1 via switch S2 and/or switch S1. In particular, when the input of the 8 k clock is inverted by Ibit1, the I transmitter 255 produces a negative simulated sinewave, $-\sin(t+\phi)$ during the time that Ibit1 remains a logic HIGH. Otherwise, the output of the I transmitter 255 is a simulated sinewave, $\sin(t+\phi)$. However, it should not be inferred that the timing of Ibit1 and the 8 k clock CLK1 must be coincident. In fact, the start and end points for Ibit1 (and Ibit0) may be advantageously shifted with respect to the 8 k clock cycle. This situation will be explained later in more detail in connection with FIGS. 5A, 5B and 6.

Ibit0 controls the state of switch S3. This bit and its effects are entirely independent of IBit1. Switch S3 controls whether the (normalized) peak amplitude of the simulated sinewave at the output of the amplifier AMP1 is 0.5 or 1.0, but has no effect on its polarity. When switch S3 is open, the normalized peak output of the amplifier is +1 or −1. When Switch S3 is closed, resistor R3 is switched into the feedback loop and the normalized peak output voltage is reduced by half, resulting in a peak value equal to +0.5 or −0.5.

In the general case, Ibit0 changes states with the digital information to be relayed to the external unit. Thus, during the symbol period, the amplitude of the simulated may be either 0.5 or 1.0, depending on the value of Ibit0. It should be understood that the state changes of Ibit0 do not have to occur at times that are coincident with the start and/or end of an 8 k clock cycle. However, the values of Ibit0 do remain constant for a full 122 microseconds, the equivalent duration of an 8 k clock cycle.

The internal implementations of the I transmitter 255 and Q transmitter 260 are typically identical. Thus, the explanation detailing the functionality of the I transmitter 255 given above applies to the Q transmitter 260. However, it should be observed that the addition of circuitry external to the Q transmitter 260 produces the necessary inversion and phase shift.

Specifically, the addition of an inverter INV2 between Qbit1 nd the input to an exclusive-OR XOR' produces an inverted output. The addition of a D-Flip Flop FF1 produces a 90-degree phase shifted version of the 8 k clock labeled 8 k90. An inverter INV3 yields an inverted version of the 16 k clock CLK2, labeled 16 k*. The result of the addition of these two elements is a 90-degree phase shift in the output of Q transmitter 260 as compared to I transmitter 255, placing the I transmitter and Q transmitter in phase quadrature.

Having described the hardware implementation of the transmitter module 205, the data encoding and transmission processes along with the advantages of the present invention will now be described in connection with FIGS. 4A through 7. Switches S1 and S2 are sequenced by signals generated by the 16 k and 32 k clocks. The resulting output waveforms are simulated sinewaves, synthesized with squarewaves, readily produced by digital circuitry in integrated circuitry.

Bit1 and Bit0 (FIG. 4A) control the polarity and magnitude, respectively, of the output of a given transmitter module 205 and, therefore modulate, the output from the amplifier gain stage 240, encoding the digital information in the output signal of the I transmitter 255. The pair of transmitters, I and Q, in phase quadrature, thus encode four bits of information during each 122 microsecond period using the modified quadrature amplitude modulation method, quadrupling the data transmission rate without increasing the clock speed of the carrier.

In particular, the quadrupling of the data rate is achieved by taking advantage of the orthogonality of I and Q components produced by the I transmitter and Q transmitter, respectively. It may be observed that the increase in performance is achieved without substantially increasing the complexity of the hardware. It should also be noted at this time that the symbol period of 122 microseconds may be advantageously shifted with respect to the 8 k clock, CLK1. This feature will now be explained more fully in connection with FIGS. 5A, 5B and 6.

Figure 5A:
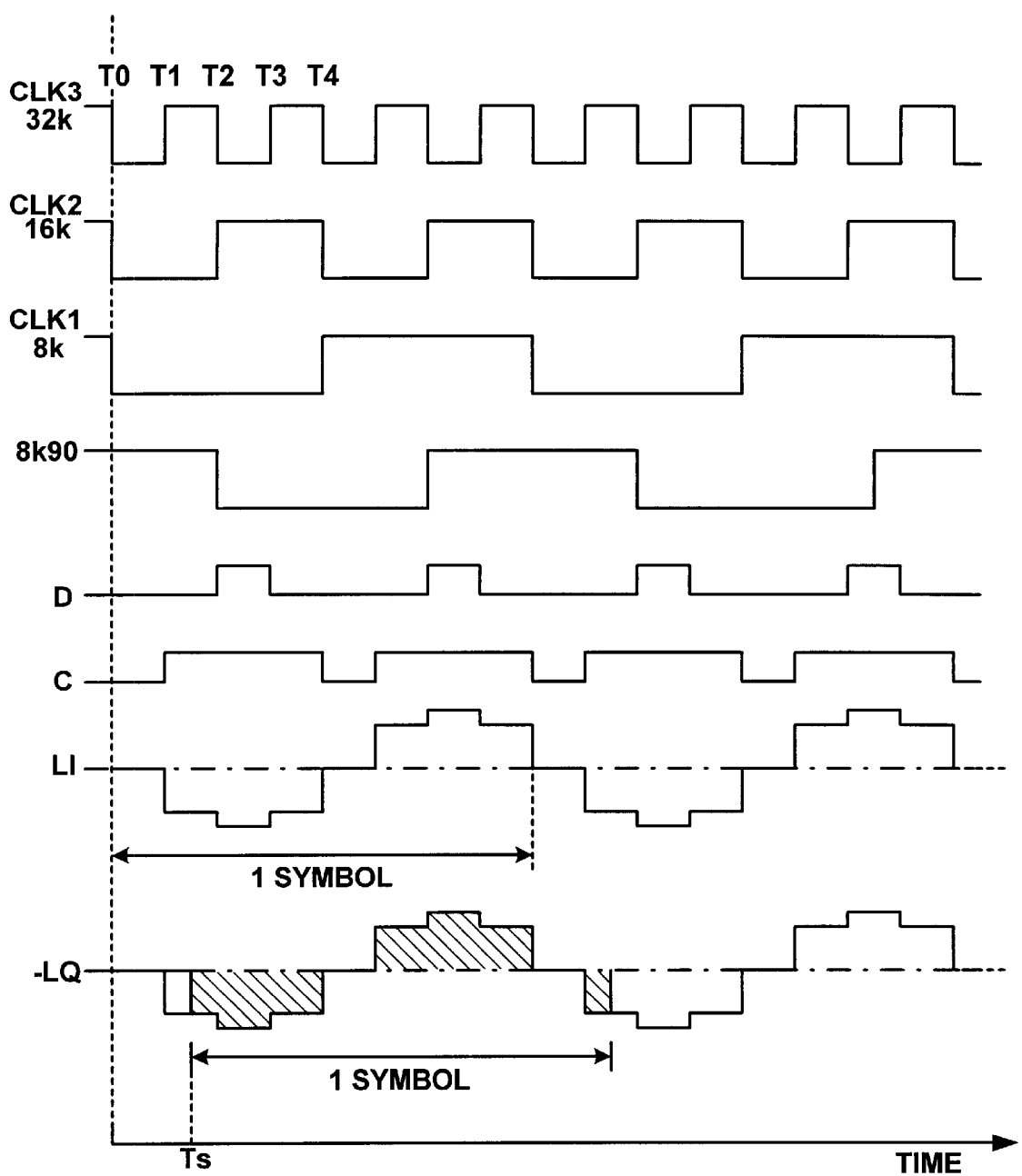
FIGS. 5A and 5B are timing diagrams illustrating key signals within the implanted unit of FIGS. 3 and 4, with FIG. 5A depicting data related to the I transmitter and FIG. 5B depicting data related to the Q transmitter.
Figure 5B:
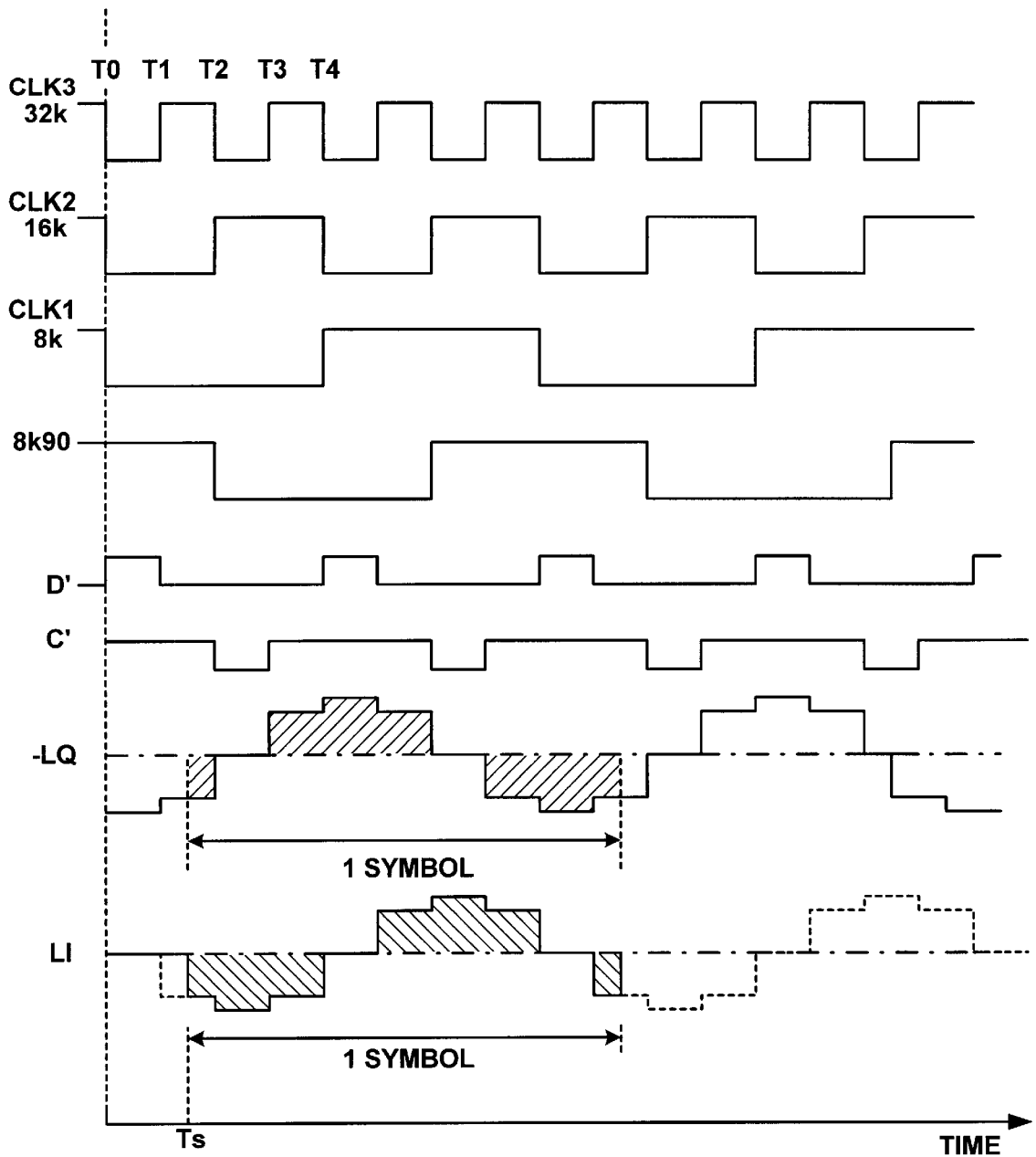

FIGS. 5A and 5B are timing diagrams depicting key signals found within the implanted unit 100 of FIGS. 4A and 4B, and implemented in the hardware illustrated in FIG. 3. FIG. 5A reflects the timing diagrams associated with the I transmitter 255, and FIG. 5B reflects the timing diagrams associated with the Q transmitter 260.

Four clock signals appear in FIG. 5A, including the 8 k clock CLK1, the 8 k clock in phase quadrature with the 8 k clock (labeled 8 k90), along with the 16 k clock CLK2, and 32 k clock CLK3. The 8 k clock CLK1 is used to control, along with Bit1, the output state of the exclusive-OR XOR1 of FIG. 4. The 8 k90 clock serves the same purpose within the Q transmitter 260, driving one of the inputs to the exclusive-OR XOR1'. The 8 k90 clock is in phase quadrature with the 8 k clock CLK1, i.e., differing in phase by 90 degrees.

Also depicted in FIG. 5A are the input waveforms to switches S1 and S2, of FIG. 4A. These waveforms are labeled D and C, respectively. In FIG. 5A, LI represents a non-modulated, synthesized sinewave, resulting exclusively from the prescribed sequencing of switches S1, S2, and an input from the 8 k clock CLK1. In particular, throughout the duration depicted, it is assumed that Bit1 and Bit0 are logic LOWs.

The timing sequence of FIG. 5A is as follows: Beginning at time T1 the output of the OR gate OR1, driven by the 32 k clock CLK3 and the 16 k clock CLK2 closes switch S2 for reducing the input resistance value from an open circuit to a value equal to R2. Referencing FIG. 4A and Table 1 above, the gain of the amplifier gain stage 240 is given by −R4/R2=−100 k/138 k=−0.725.

One CLK3 half-period later, at T2, switch S1 closes and the input resistance drops to a value equal to the parallel combination of resistors R1 and R2. The gain of the amplifier gain stage 240 with switch S3 open is 1. The amplifier gain stage 240 remains in this state for another CLK3 half-period before switch S1 re-opens at T3, dropping the input resistance 250 to R2, and the gain is once again −0.725. At T4, switch S2 opens and the input resistance 250 goes to an open circuit, dropping the gain to 0. The sequence repeats as the 8 k clock goes HIGH. The output of the amplifier AMP1 is positive on this half cycle as the output of the exclusive-OR has changed states due to the change in the state of the 8 k clock CLK1. The duration of one period of the simulated sinewave is 122 microseconds.

FIG. 5B conveys corresponding information about key signals in the Q transmitter 260. The control signals at nodes C' and D' depict the logic sequence required to synthesize the simulated sinewave −LQ. The clock cycles of the internal clocks are displayed to illustrate the relative timing and to facilitate the understanding of the synthesis, similar to that given above. For comparison of phase and timing, signal LI, the synthesized sinewave from the I transmitter 255, has been reproduced in FIG. 5B. Readily apparent is the phase quadrature between LI and −LQ.

An important consideration in the implementation of the present invention is the choice of symbol delimiters at the start and end of a symbol period. An appropriate choice reduces the noise and other deleterious effects associated with step-function changes. One preferred choice of symbol timing is illustrated by means of superposed cross-hatching on the LI and −LQ waveforms of FIGS. 5A and 5B. The symbol periods of the I and Q transmitters 255 and 260 are coincident in time, though obviously not in phase, but rather maintaining relative phase quadrature.

It should also be noted that the start of the symbol period for both the I and Q carriers is shifted 45 degrees with respect to the 8 k clock. It is during this symbol period that the information encoded in the signal (Ibit1, Ibit0, Qbit1, Qbit0) remains constant. That is, Bit1 and Bit0 are constant during this period, but not during the period corresponding to one cycle of the 8 k clock. The beginning of the first LQ symbol period is labeled Ts in FIGS. 5A and 5B. The beginning of the 8 k clock cycle is labeled T0.

Figure 6A:
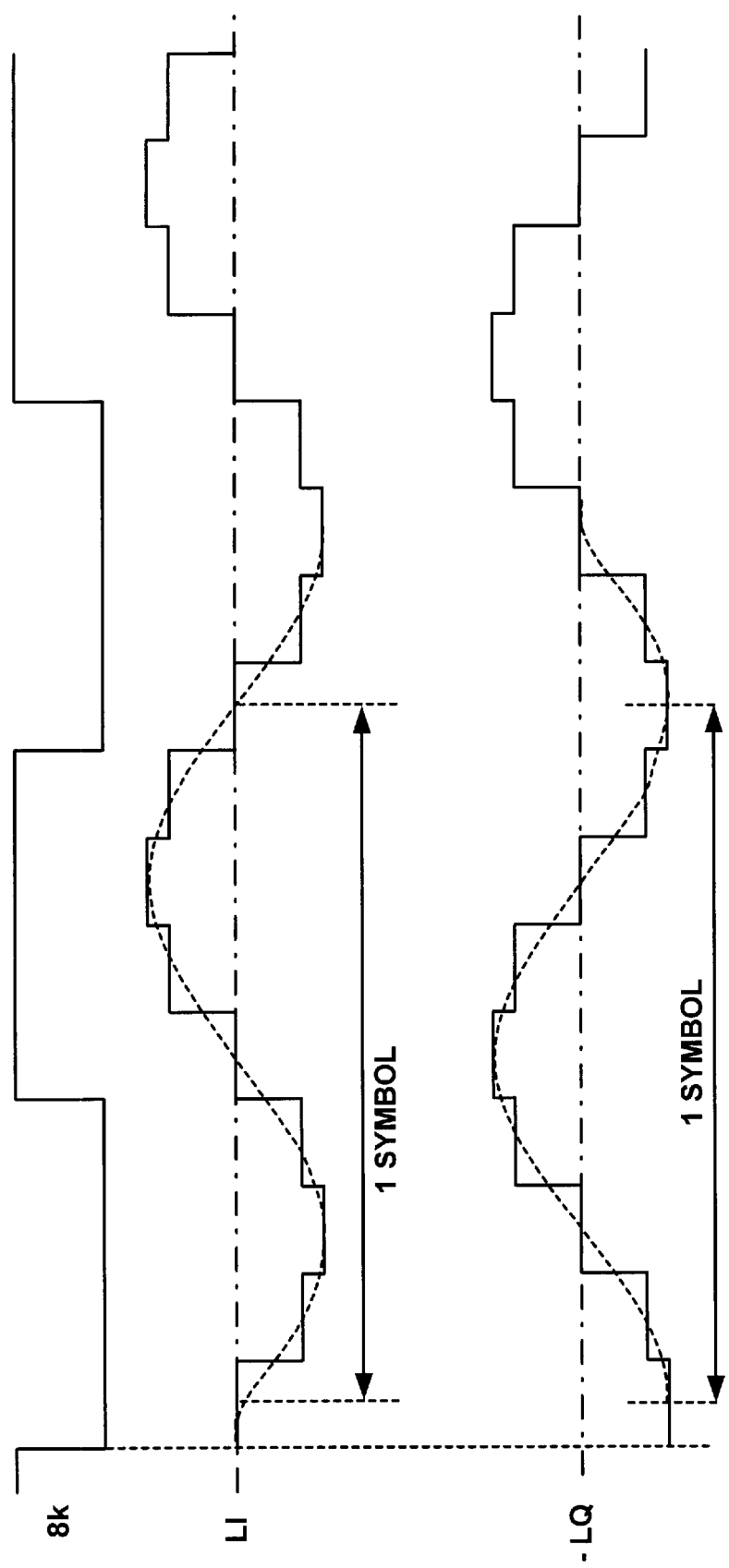
FIGS. 6A and 6B represent detailed timing diagrams depicting the relative timing of I and Q symbols with respect to an 8 k clock of the implanted device of FIGS. 1 and 4.
Figure 6B:
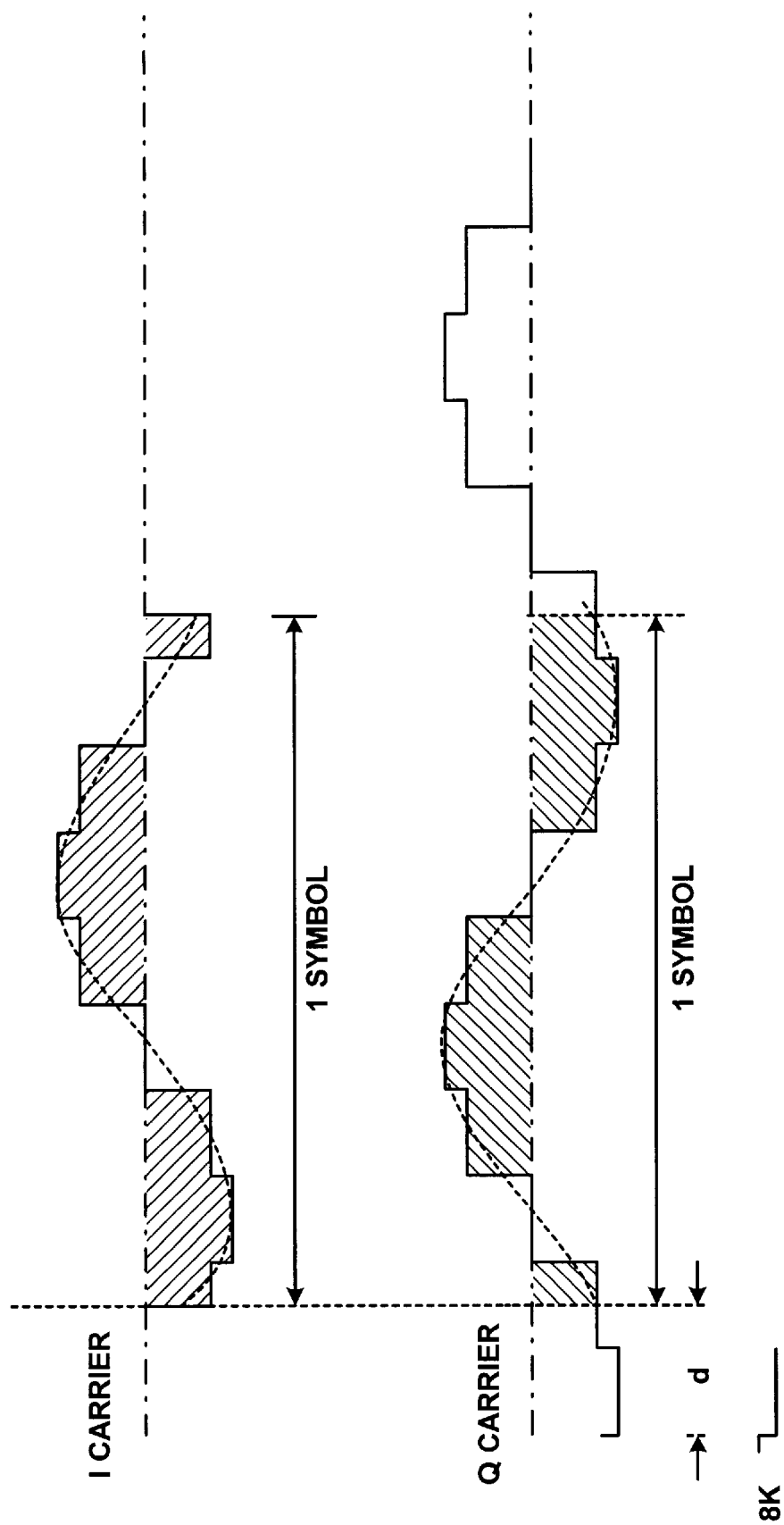

FIGS. 6A and 6B serve to further illustrate the efficacy of the preferred choice in symbol timing relative to the 8 k clock cycles. In practice, the symbol delimiters or zero crossings (i.e., start and end of the symbol period) with respect to the 8 k clock can be selected in several ways. One choice, depicted in FIG. 6A is to have the I carrier in phase with the 8 k clock and to begin simultaneous to the start of the 8 k clock cycle. The synthesized sinewave, with an actual sinewave superposed for emphasis and clarity, displays no step function behavior at the beginning or end of the symbol period. This selection would always have zero amplitude at the start and end of the I symbol, an advantageous situation. Such is not the case for the symbol generated by the Q transmitter 260.

The Q carrier starts at the same time as the I carrier, but has a 90 degrees shift. The Q carrier, as shown, would jump full amplitude in the positive or negative direction at the symbol start and end when Qbit1 goes from 0 to 1 or from 1 to zero, and would generate a large number of potentially deleterious harmonics. A compromise can be reached by selecting the symbol delimiting illustrated in FIG. 6B, which includes delaying the symbol by a delay period, d, of 22.8 μs with respect to 8 k CLK1 start.

At the symbol start, the worst-case amplitude jump is now reduced and is the same on both the I and Q symbols. By shifting both the I and Q symbols 45 degrees with respect to the 8 k clock, the noise due to harmonics, generated by step functions, can be reduced, for example: ((45 degrees/360 degrees)×122 μs=15.25 μs, and add ½ step duration of 122 μs/16=7.625 μs). The one-symbol durations are illustrated by the cross-hatched regions of signals LI and −LQ in FIGS. 5A and 5B. These regions correspond to the cross-hatched regions shown in FIG. 6B.

Figure 7:
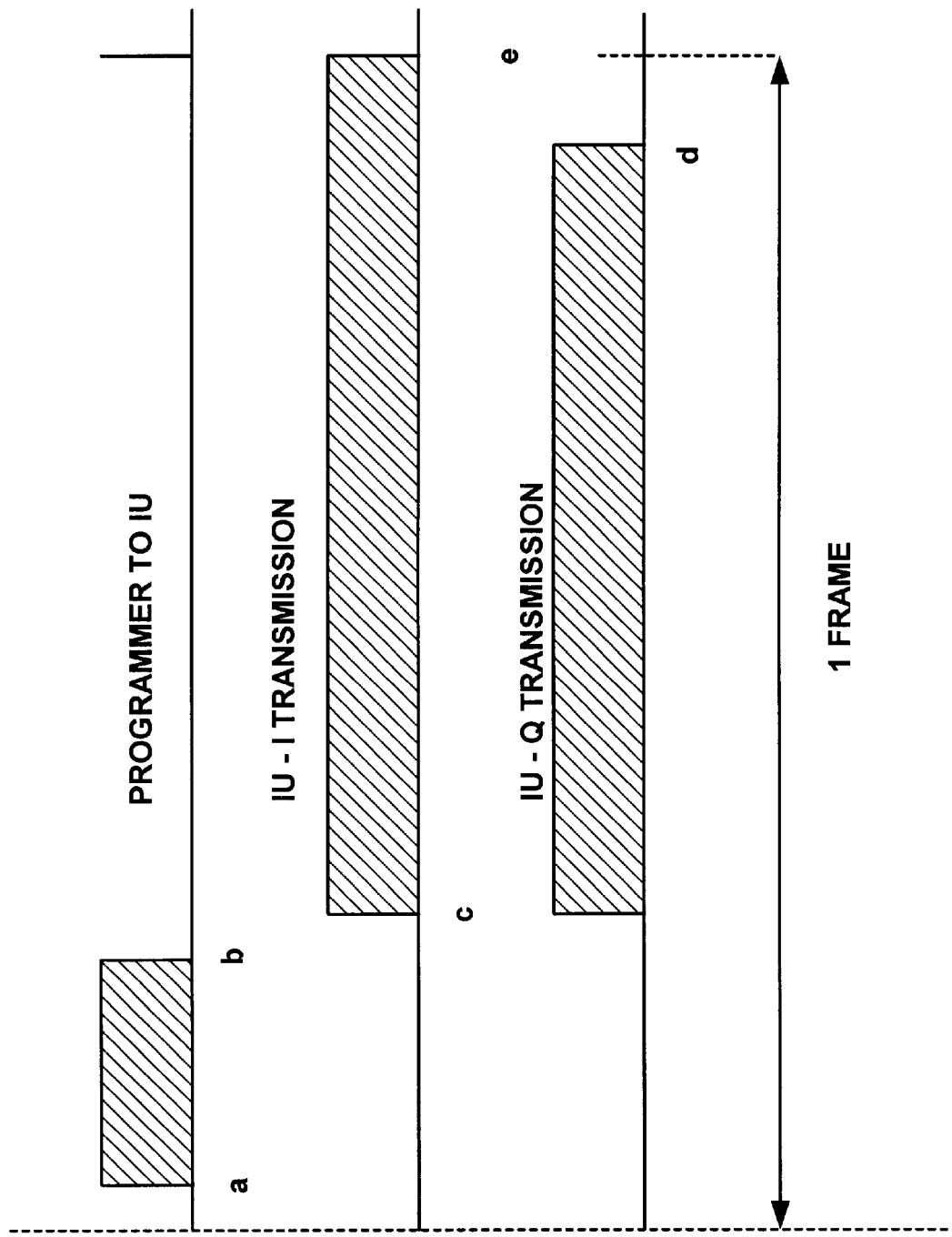
FIG. 7 represents data transferred between the external unit of FIG. 3 and the corresponding implanted unit of FIGS. 3 and 4, illustrating a methodology for achieving phase locking and automatic gain control within the external unit.

FIG. 7 illustrates yet another implementation feature according to the present invention. When both the I and Q signals are combined, they typically require complicated circuitry in the external device 102 to allow the phase locked loop (PLL) to extract the I and Q phases. To simplify this task, for a portion of the transmission period, labeled d-e in FIG. 7, the implanted unit 100 transmits at full amplitude only the I component. Thus, the phase locked loop can easily acquire and lock onto I transmitter phase and frequency. The phase of the Q transmitter 260, being in phase quadrature, is then simply a 90-degree shift from the I phase. Transmission at full amplitude allows the automatic gain control (AGC) within the external device 102 to be simplified in its implementation as well, since it is able to lock onto a signal with no interference, with a larger magnitude and a larger signal-to-noise ratio.

The unit of time depicted in FIG. 7 is referred to as one frame and is repeated as long as the communication is open. Within this frame, the external device 102 communicates with the implanted unit 100. In turn, the implanted unit 100 transmits four bits information per symbol to the external unit 102. Early termination of the Q transmitter symbols as described above, ensures that the external device 102 is able to successfully receive and de-modulate the transmitted information.

Thus, a high speed telemetry system has been provided, which uses a modified QAM transmission of data from the implanted unit to the external device for achieving four times the conventional data transfer rate, while maintaining the simplicity of the design. The phase locking and gain control in the telemetry system is achieved by transmission at full amplitude, of only the I component for a small fraction of the received frame signal. The telemetry system can use Pulse Amplitude modulation to effect communication from the external unit to the implanted unit.

While certain preferred embodiments of the invention have been described, these embodiments have been presented by way of example only, and are not intended to limit the scope of the present invention.

What is claimed is:

1. A telemetry system for use in an implantable cardiac stimulation device, comprising:
   a telemetry coil;
   a transmitter module, coupled to the telemetry coil, that transmits data at a predetermined transmission rate over the telemetry coil, the transmitter module configured to perform a modified quadrature amplitude modulation process;
   a controller coupled to the transmitter module that provides the transmitter module with a squarewave input clock signal, the controller further causing the transmitter module to execute the modified quadrature amplitude modulation process to convert the squarewave signal into simulated sinewave symbols, and further to encode data bits of information in each of the simulated sinewave symbols.

2. The telemetry system according to claim 1, wherein the data transmission rate is approximately 32 kbps.

3. The telemetry system according to claim 1, wherein the transmitter module includes a switch circuit coupled to, and selectively regulated by the input clock signal.

4. The telemetry system according to claim 3, wherein the transmitter module further includes an inverting amplifier stage connected intermediate the switch circuit and the telemetry coil, to generate the simulated sinewave symbols.

5. The telemetry system according to claim 4, wherein the inverting amplifier stage includes an input resistance stage having a variable resistance that is determined by the switch circuit.

6. The telemetry system according to claim 5, wherein the switch circuit includes a first switch and a second switch that are connected to the input resistance stage.

7. The telemetry system according to claim 6, wherein the squarewave input clock signal includes a first pulse train at a frequency of approximately 8 kbps.

8. The telemetry system according to claim 7, wherein the squarewave input clock signal includes a second pulse train at a frequency of approximately 16 kbps.

9. The telemetry system according to claim 8, wherein the squarewave input clock signal includes a third pulse train at a frequency of approximately 32 kbps.

10. The telemetry system according to claim 4, wherein the transmitter module encodes the data bits of information by changing the amplitude and polarity of the simulated sinewave symbols.

11. The telemetry system according to claim 10, wherein the transmitter module includes an I transmitter that generates an I component to be transmitted, and a Q transmitter that generates a Q component to be transmitted; and wherein the I component and the Q component are orthogonal with phases in quadrature to enable an external decoder to decode the input data.

12. The telemetry system according to claim 11, wherein each of the I transmitter and the Q transmitter implements a two-bit modulation of the data to be transmitted.

13. The telemetry system according to claim 12, wherein the transmitter module encodes four data bits Ibit1, Ibit0, Qbit1, Qbit0 during one symbol period.

14. The telemetry system according to claim 13, wherein the symbol period is approximately 122 μs.

15. The telemetry system according to claim 13, wherein the data bits Ibit1 and Ibit0 are encoded in an I transmitter signal; and wherein the data bits Qbit1 and Qbit0 are encoded in a Q transmitter using a carrier frequency that is 90 degrees out of phase with respect to a carrier frequency used by the I transmitter.

16. The telemetry system according to claim 15, wherein the inverting amplifier stage feeds the four data bits Ibit1, Ibit0, Qbit1, Qbit0 into a telemetry coil for transmission.

17. The telemetry system according to claim 16, wherein the data bit Ibit1 determines the polarity of the simulated sinewave symbols of the I transmitter.

18. The telemetry system according to claim 17, wherein the data bit Ibit0 independently controls the amplitude of the simulated sinewave symbols of the I transmitter.

19. The telemetry system according to claim 17, wherein the data bit Qbit1 determines the polarity of the simulated sinewave symbols of the Q transmitter.

20. The telemetry system according to claim 19, wherein the data bit Qbit0 independently controls the amplitude of the simulated sinewave symbols of the Q transmitter.

21. The telemetry system according to claim 11, wherein the transmitter module shifts starting points of the I and Q components by a predetermined value with respect to the input clock signal.

22. The telemetry system according to claim 21, wherein the input clock signal includes a first pulse train at a frequency of approximately 8 kbps; and wherein the transmitter module shifts the starting points of the I and Q components by 45 degrees with respect to the 8 kbps input clock signal.

23. In a telemetry system for use in an implantable cardiac stimulation device, a method of telemetering data comprising the steps of:

providing a squarewave signal at a predetermined frequency;

processing the squarewave signal utilizing a modified quadrature amplitude modulation process to thereby generate simulated sinewaves, telemetering the simulated sinewaves to a remote receiver.

24. The method of claim 23 comprising the step of encoding data bits of information into the simulated sinewaves.

25. The method of claim 24 whereby the encoding step includes the step of changing the amplitude and polarity of the simulated sinewaves.

26. The method of claim 25 wherein the step of processing the squarewave signal includes the step of generating a pair of simulated sinewaves in phase quadrature.

27. The method of claim 26 wherein the step of encoding includes the step of encoding two data bits of information in each one of the pair of simulated sinewaves.

28. The method of claim 27 wherein the step of encoding further includes the step of utilizing one of the two data bits of information for changing the magnitude of a respective simulated sinewave and the other bit of information for changing the polarity of said respective simulated sinewave.

29. The method of claim 28 wherein the simulated sinewaves have a predefined period, the encoding step further comprising the step of encoding four data bits of information during said period, two of said data bits being encoded in each one of the simulated sinewaves.

30. The method of claim 29 comprising the step of utilizing a predetermined frequency of 8192 Hz.

31. A telemetry system for use in an implantable cardiac stimulation device, comprising:

telemetry coil means for telemetering data;

transmitter means for transmitting data to be telemetered over the telemetry coil means at a predetermined transmission rate; and control means for providing the transmitter means with a squarewave input clock signal, the transmitter means utilizing the input clock signal for executing a modified quadrature amplitude modulation process for converting the squarewave input clock signal into simulated sinewave symbols, the transmitter means further for encoding data bits of information in each of the simulated sinewave symbols.

32. The telemetry system according to claim 31, wherein the transmitter means includes an inverting amplifier means for generating the simulated sinewave symbols.

33. The telemetry system according to claim 31, wherein the transmitter means includes an I transmitting means for generating an I component, and a Q transmitting means for generating a Q component; and wherein the I component and the Q component are orthogonal with phases in quadrature to enable a decoding means to decode input data.

34. The telemetry system according to claim 33, wherein the transmitter means encodes four data bits Ibit1, Ibit0, Qbit1, Qbit0 during a symbol period;

wherein the data bits Ibit1 and Ibit0 are encoded in an I transmitter signal; and wherein the data bits Qbit1 and Qbit0 are encoded in a Q transmitter using a carrier frequency that is 90 degrees out of phase with respect to a carrier frequency used by the I transmitter.

* * * * *